(12) United States Patent
DeHoff et al.

(10) Patent No.: US 6,312,920 B1
(45) Date of Patent: Nov. 6, 2001

(54) SAM OPERON

(75) Inventors: Bradley Stuart DeHoff; Paul Robert Rosteck, Jr., both of Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 08/955,957

(22) Filed: Oct. 22, 1997

Related U.S. Application Data

(60) Provisional application No. 60/030,898, filed on Nov. 13, 1996, now abandoned.

(51) Int. Cl.$^7$ .................................................. C12P 21/06
(52) U.S. Cl. ..................... 435/69.1; 435/471; 435/183; 435/193; 435/252.3; 435/252.33; 435/320.1; 530/350; 530/371; 536/23.1; 536/23.2; 536/23.7; 536/23.74; 536/24.1
(58) Field of Search .................. 536/23.1, 24.1, 536/320.1, 23.2, 23.7, 23.74; 435/252.3, 252.33, 252.35, 6, 41, 69.1, 106, 113, 183, 193, 440, 471, 320.1; 530/350, 371

(56) References Cited

U.S. PATENT DOCUMENTS 5,672,497 * 9/1997 Cox et al. .......................... 435/320.1

FOREIGN PATENT DOCUMENTS

| | | |
|---|---|---|
| 0 189 322 A2 | 1/1986 | (EP) . |
| 0 647 712 A1 | 10/1993 | (EP) . |
| WO 93/10223 | 5/1993 | (WO) . |
| WO 94/08014 * | 4/1994 | (WO) . |

OTHER PUBLICATIONS

Fishman et al. Proceedings of the National Academy of Sciences, USA. vol. 84, pp. 8248–8252, Dec. 1997.*
M. L. Dickens, et al. "Cloning, Sequencing and Analysis of Aklaviketone Reductase from *Streptomyces sp.* Strain C5." *Journal of Bacteriology* 178(11) :3384–3388 (Jun. 1996).
R. H. Baltz and E. T. Seno. "Genetics of *Streptomyces Fradiae* and Tylosin Biosynthesis." *Ann. Rev. Microbiol.* 42:547–74 (1988).
N. J. Bauer, et al. "Purification, Characterization, and Kinetic Mechanism of S–Adenoxyl–L–methionine:Macrocin O–Methyltransferase from *Streptomyces fradiae*." *The Journal of Biological Chemistry* 263(30) :15619–15625 (Oct. 25, 1988).
M. Bierman, et al. "Plasmid cloning vectors for the conjugal transfer of DNA from *Escherichia coli* to *Streptomyces* spp." *Gene* 116:43–49 (1992).

* cited by examiner

*Primary Examiner*—Remy Yucel
(74) *Attorney, Agent, or Firm*—Charles E. Cohen; Tina M. Tucker; Thomas D. Webster

(57) ABSTRACT

The invention provides isolated nucleic acid compounds encoding a novel SAM synthetase of *Streptomyces fradiae*. Also provided are vectors and transformed heterologous host cells for expressing the SAM synthetase and a method for preparing S-adenosylmethionine from recombinant host cells transformed with the SAM synthetase gene.

36 Claims, 2 Drawing Sheets

SAM OPERON

We hereby claim the benefit under Title 35, United States Code, §119(e) of U.S. provisional patent application No. 60/030,898 filed Nov. 13, 1996 now abandoned.

BACKGROUND OF THE INVENTION

This invention relates to recombinant DNA technology. In particular the invention pertains to the cloning of the SAM operon genes from *Streptomyces fradiae* and the use of said genes and their encoded proteins to produce S-adenosylmethionine (SAM) in a recombinant host.

S-adenosylmethionine is a product of natural origin found in all living organisms. SAM is a product of considerable importance for its role in biological reactions such as transmethylations. While the enzymes that catalyze these reactions are varied in their substrate specificity they are practically universal in their requirement of S-adenosylmethionine as the ultimate methyl group donor. Some methyl transfer reactions are important in the synthesis of certain antibiotics, such as tylosin.

Tylosin is a macrolide antibiotic composed of a 16-membered branched lactone, tylactone, and residues of three attached sugars, mycaminose, mycarose, and mycinose. Tylosin is produced commercially by *Streptomyces fradiae* (ATCC 19609; NRRL 2702) and is used as an animal growth promotant and veterinary antibiotic. The multi-step biosynthesis of tylosin has been studied both physiologically and genetically (See generally, R. H. Baltz and E. T. Seno, "Genetics of *Streptomyces fradiae* and tylosin biosynthesis." Ann. Rev. Microbiol. 42, 547–74 (1988)). At least 13 biosynthetic genes and 2 regulatory genes are necessary for normal production of tylosin. Tylosin synthesis requires multiple methylation reactions, the last two of which are rate-limiting. In the last step a specific methyltransferase catalyzes the transfer of a methyl group from SAM to the tylosin precursor molecule, macrocin. Thus, the availability of SAM as the methyl group donor is essential in the synthesis of tylosin.

S-adenosylmethionine is produced when an adenosyl group is transferred from ATP to methionine. SAM is synthesized in the cell by the action of three enzymes encoded by the SAM operon—SAM synthetase, methyl transferase (MT), and methylene tetrahydrofolate reductase (MTHR).

SUMMARY OF THE INVENTION

The present invention provides, inter alia, isolated nucleic acid molecules comprising the SAM operon from *Streptomyces fradiae*. The invention also provides the protein products encoded by the SAM operon, in substantially purified form.

Having the cloned SAM operon of *Streptomyces fradiae* enables the production of S-adenosylmethionine in recombinant host cells.

In one embodiment the present invention relates to an isolated nucleic acid that encodes SAM synthetase from *Streptomyces fradiae*, said nucleic acid comprising nucleotide residues 986 through 2209 of the nucleotide sequence identified as SEQ ID NO. 1.

In another embodiment the present invention relates to an isolated nucleic acid that encodes MT from *Streptomyces fradiae*, said nucleic acid comprising nucleotide residues 2241 through 3341 of SEQ ID NO.1.

In another embodiment the present invention relates to an isolated nucleic acid that encodes MTHR from *Streptomyces fradiae*, said nucleic acid comprising nucleotide residues 3338 through 4255 of SEQ ID NO.1.

In another embodiment the present invention relates to a novel SAM synthetase from *Sreptomyces fradiae* in substantially purified form comprising the sequence identified as SEQ ID NO. 2.

In still another embodiment the present invention relates to a novel MT from *Streptomyces fradiae* in substantially purified form comprising the sequence identified as SEQ ID NO. 3.

In yet another embodiment the present invention relates to a novel MTHR from *Streptomyces fradiae* in substantially purified form comprising the sequence identified as SEQ ID NO.5.

In a further embodiment the present invention relates to a ribonucleic acid molecule encoding SAM synthetase, said ribonucleic acid molecule comprising residues 986 through 2209 of the sequence identified as SEQ ID NO. 6:

In yet another embodiment, the present invention relates to a recombinant DNA vector that incorporates the *Streptomyces fradiae* SAM operon genes in operable linkage to gene expression sequences enabling said genes to be transcribed and translated in a host cell.

In still another embodiment the present invention relates to homologous or heterologous host cells which have been transformed or transfected with one or more of the cloned SAM operon genes from *Streptomyces fradiae* such that said gene(s) is/are expressed in the host cell.

In a still further embodiment, the present invention relates to a method for producing S-adenosylmethionine in recombinant host cells transformed with the *S. fradiae* SAM synthetase gene.

DEFINITIONS

Figure 1:
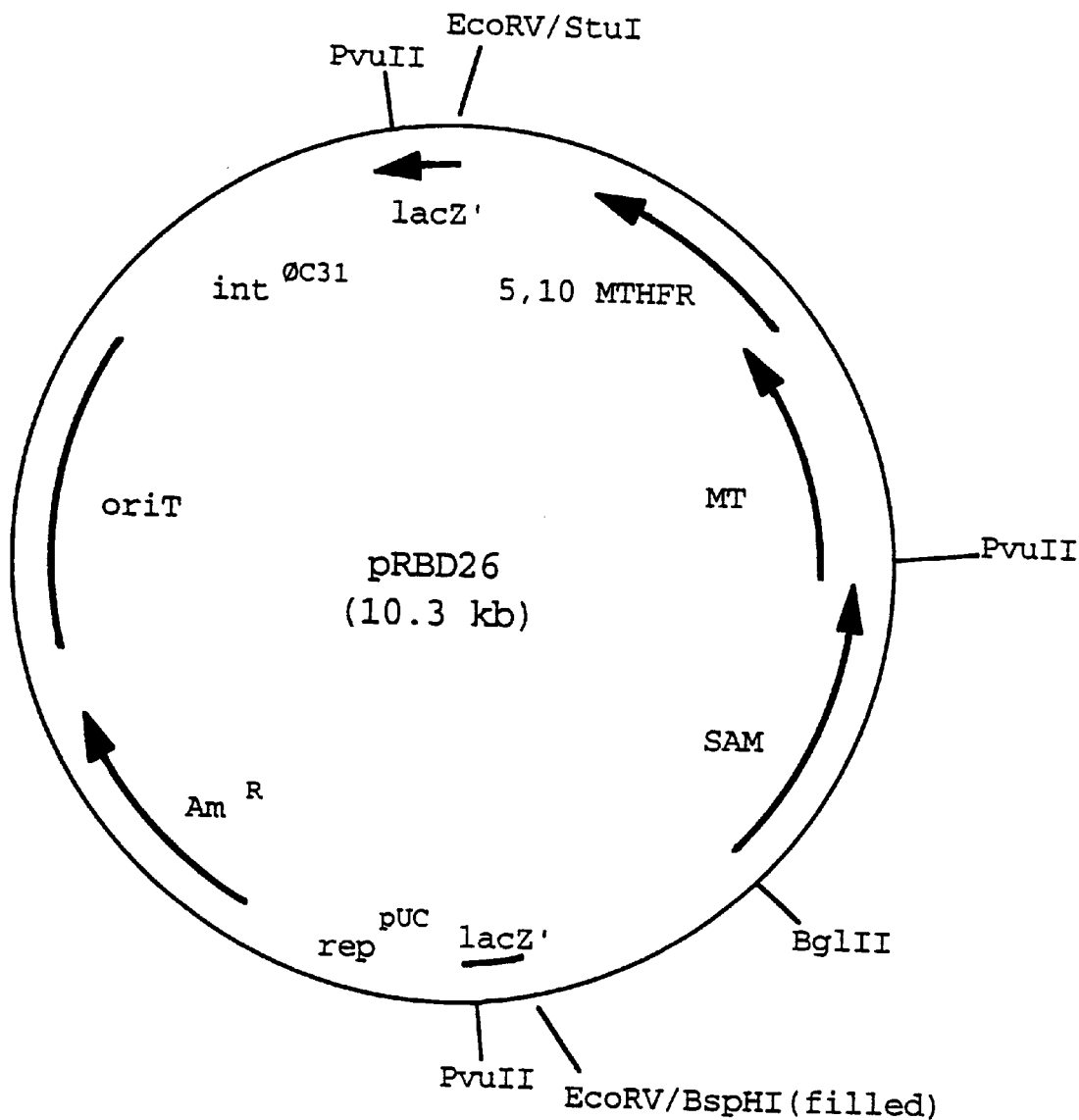
FIG. 1. Plasmid pRBD26, useful for expression of the *Streptomyces fradiae* SAM synthetase gene of the present invention in the homologous host cell or other actinomycete.

The term "operon" as used herein refers to a genetic unit comprising a region of a chromosome having one or more structural genes said unit producing a messenger RNA molecule that may or may not be polycistronic (i.e. encoding more than one protein). Transcription of said RNA is under the control of a single promoter.

"SAM" refers to S-adenosylmethionine.

"MT" refers to methyltransferase.

"THF" refers to tetrahydrofolate.

"MTHR" refers to methylene tetrahydrofolate reductase.

"ATP" refers to adenosine triphosphate.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with a complementary nucleic acid compound.

The term "hybridization" as used herein refers to a process in which a single-stranded nucleic acid molecule joins with a complementary strand through nucleotide base pairing. "Selective hybridization" refers to hybridization under conditions of high stringency. The degree of hybridization depends upon, for example, the degree of complementarity, the stringency of hybridization, and the length of hybridizing strands.

The term "stringency" refers to hybridization conditions. High stringency conditions disfavor non-homologous base-pairing. Low stringency conditions have the opposite effect. Stringency may be altered, for example, by temperature and salt concentration.

DETAILED DESCRIPTION

Figure 2:
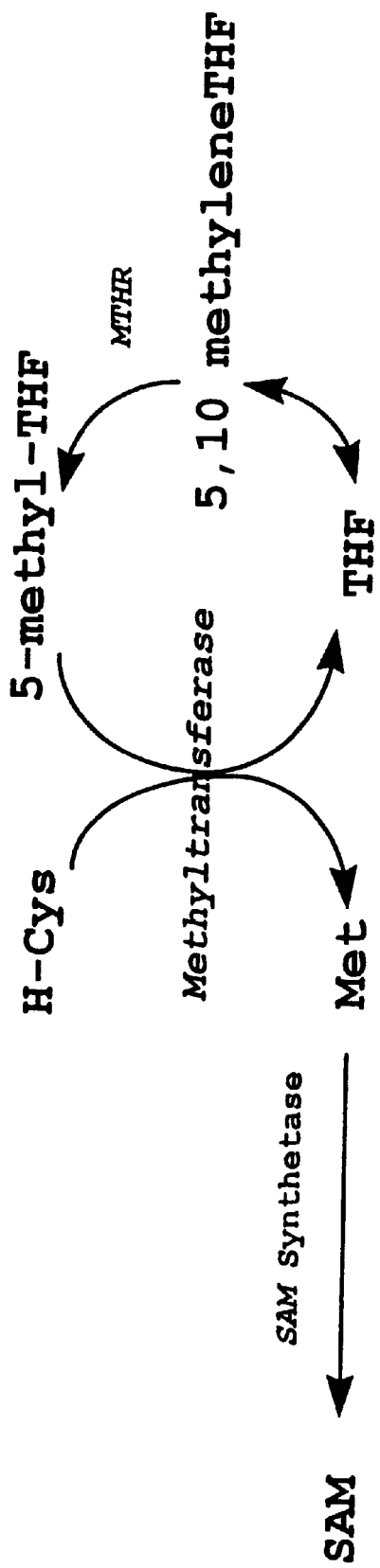
FIG. 2. Activated methyl cycle.

The SAM operon of the present invention comprises three genes encoding SAM synthetase, MT, and MTHR. Together these enzymes comprise the so-called "activated methyl cycle" which produces S-adenosylmethionine (see FIG. 2). The "activated methyl cycle" provides the methyl groups required for the final steps in tylosin production.

The SAM synthetase gene disclosed herein comprises a DNA sequence of 1224 nucleotide base pairs (residues 986 through 2209 of SEQ ID NO. 1). The MT gene disclosed herein comprises a DNA sequence of 1101 nucleotide base pairs (residues 2241 through 3341 of SEQ ID NO.1). The MTHR gene disclosed herein comprises a DNA sequence of 918 nucleotide base pairs (residues 3338 through 4255 of SEQ ID NO.4). There are no intervening sequences in the SAM operon. The 5' end of the MTHR gene overlaps (in another reading frame) with four nucleotide residues at the 3' end of the MT gene. Specifically, the "TGA" stop codon of the MT gene ends at residue 3341 of SEQ ID NO.4, while the "GTG" start codon of the MTHR gene begins at residue 3338 of SEQ ID NO.4. Those skilled in the art will recognize that owing to the degeneracy of the genetic code (i.e. 64 codons which encode 20 amino acids), numerous "silent" substitutions of nucleotide base pairs could be introduced into this sequence without altering the identity of the encoded amino acid(s) or protein product. All such substitutions are intended to be within the scope of the invention.

The SAM synthetase of the present invention, designated SEQ ID NO.2, comprises a protein of 407 amino acid residues. The MT of the present invention, designated SEQ ID NO.3, comprises a protein of 366 amino acid residues. The MTHR of the present invention, designated SEQ ID NO.5, comprises a protein of 305 amino acid residues.

Gene Isolation Procedures

Those skilled in the art will recoginze that the gene of the present invention may be obtained by a plurality of applicable genetic and recombinant DNA techniques including, for example, polymerase chain reaction (PCR) amplification, or de novo DNA synthesis. (See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the SAM operon genes of *Streptomyces fradiae* comprising the present invention or fragments thereof could be isolated by PCR amplification of *Streptomyces fradiae* genomic DNA or cDNA using oligonucleotide primers targeted to a suitable region of SEQ ID NO. 1. The coding regions of the MT and MTHR genes are, respectively, 2241 through 3341, and 3338 through 4255 of SEQ ID NO.1. Methods for PCR amplification are widely known in the art. See e.g. *PCR Protocols: A Guide to Method and Application,* Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn.). Amplification of a DNA fragment of the correct size can be detected most conveniently by agarose gel electrophoresis.

Protein Production Methods

One embodiment of the present invention relates to the substantially purified SAM operon proteins or fragments thereof encoded by the genes disclosed herein.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be produced by recombinant DNA methods using the cloned SAM operon genes of *Streptomyces fradiae* disclosed herein. Recombinant methods are preferred if a high yield is desired. Expression of said cloned genes can be carried out in a variety of suitable host cells well known to those skilled in the art. In a recombinant method, a gene is introduced into a host cell by any suitable means, well known to those skilled in the art. While chromosomal integration of the cloned SAM operon genes is within the scope of the present invention, it is preferred that the genes be cloned into a suitable extra-chromosomally maintained expression vector, the coding region of the genes in operable linkage to a constitutive or inducible promoter.

The basic steps in the recombinant production of the SAM operon enzymes, SAM synthetase, MT, or MTHR of the present invention are:

a) constructing a natural, synthetic or semi-synthetic DNA encoding said enzyme(s);

b) integrating said DNA into an expression vector in a manner suitable for expressing said enzyme(s), as the natural protein product or as a fusion protein;

c) transforming or otherwise introducing said vector into an appropriate eucaryotic or prokaryotic host cell forming a recombinant host cell, d) culturing said recombinant host cell in a manner to express said enzyme(s); and e) recovering and substantially purifying said enzyme(s) by any suitable means, well known to those skilled in the art.

Expressing Recombinant *S. fradiae* SAM Operon in a Procaryotic or Eucaryotic Host Cell In general, procaryotes are used for cloning DNA sequences and for constructing the vectors of the present invention. Procaryotes may also be employed in the production of the protein of the present invention. For example, the *Escherichia coli* K12 strain 294 (ATCC No. 31446) is particularly useful for the prokaryotic expression of foreign proteins. Other strains of *E. coli*, bacilli such as *Bacillus subtilis*, enterobacteriaceae such as *Salmonella typhimurium* or *Serratia marcescans*, various Pseudomonas species and Actinomycetes, such as *Streptomyces fradiae, Streptomyces coelicolor*, and *Streptomyces lividans*, may also be employed as host cells in the cloning and expression of the recombinant proteins of this invention.

Promoter sequences suitable for driving the expression of genes in procaryotes include b-lactamase [e.g. vector pGX2907, ATCC 39344, contains a replicon and b-lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Useful promoters for driving gene expression in a Streptomyces host are known. For example, the snpR promoter is useful for gene expression in Streptomyces (See e.g. *6th Conference on the Genetics and Molecular Biology of Industrial Microorganisms*, Oct. 20–24, 1996, Bloomington, Ind., Abstract P37). Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. The cloned DNA comprising the SAM operon of the present invention carries the endogenous promoter in the region comprising nucleotide residues 1 through 985 of SEQ ID NO.1. This promoter will function in other Actinomycetes. These examples are illustrative rather than limiting.

The protein of this invention may be synthesized either by direct expression or as a fusion protein comprising the protein of interest as a translational fusion with another protein or peptide which may be removable by enzymatic or chemical cleavage. Expression as a fusion protein may prolong the half-life, increase the yield of the desired peptide, or provide a convenient means of purifying the protein. A variety of peptidases (e.g. enterokinase and thrombin) cleave a polypeptide at specific sites or digest peptides from the amino or carboxy termini (e.g. diaminopeptidase). Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes*, American Chemical Society, Washington, D.C. (1990).

In addition to procaryotes, a variety of mammalian cell systems and eucaryotic microorganisms such as yeast are suitable host cells. The yeast *Saccharomyces cerevisiae* is the most commonly used eucaryotic microorganism. A number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced SAM Operon Enzymes

An expression vector carrying any of the cloned SAM operon genes as claimed herein is transformed or transfected into a suitable host cell using standard methods. Cells which contain the vector are propagated under conditions suitable for expression of the SAM operon enzyme(s) encoded by the vector. As an example, a vector-bound SAM synthetase gene is placed under the control of an inducible promoter. Suitable growth conditions would incorporate an appropriate inducer. Recombinantly-produced SAM synthetase may then be purified from cellular extracts of transformed cells by any suitable means, well known to those skilled in the art.

In a preferred process for protein purification the gene encoding the SAM operon enzyme of the present invention is modified at the 5' end to incorporate several histidine residues at the amino terminus of the encoded protein product. The "His-tag" enables a single-step protein purification method referred to as "immobilized metal ion affinity chromatography" (IMAC), essentially as described in U.S. Pat. No. 4,569,794 which hereby is incorporated by reference. The IMAC method enables rapid isolation of substantially pure protein starting from a crude cellular extract.

Other embodiments of the present invention comprise isolated nucleic acid sequences which encode SEQ ID NO:2, SEQ ID NO.3, and SEQ ID NO.5. As skilled artisans will recognize, the amino acid compounds of the invention can be encoded by a multitude of different nucleic acid sequences because most of the amino acids are encoded by more than one codon due to the degeneracy of the genetic code. Because these alternative nucleic acid sequences would encode the same amino acid sequences, the present invention further comprises these alternate nucleic acid sequences.

Nucleic acid sequences encoding the proteins of the invention may be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

In an alternative and preferred methodology, namely PCR, the DNA sequence comprising a portion or all of SEQ ID NO:1 can be generated from *Streptomyces fradiae* genomic DNA using suitable oligonucleotide primers complementary to SEQ ID NO:1 or region therein, as described in U.S. Pat. No. 4,889,818, which hereby is incorporated by reference. Suitable protocols for performing the PCR are widely known and are disclosed in, for example, PCR *Protocols: A Guide to Method and Applications,* Ed. Michael A. Innis et al., Academic Press, Inc. (1990).

The ribonucleic acids of the present invention may be prepared using the polynucleotide synthetic methods discussed supra, or they may be prepared enzymatically using RNA polymerase to transcribe a suitable DNA template. The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:6.

The present invention also provides probes and primers useful for a variety of molecular biology techniques including, for example, hybridization screens of genomic or subgenomic libraries. A nucleic acid compound comprising SEQ ID NO:1, SEQ ID NO:6 or a complementary sequence thereof, or a fragment thereof, and which is at least 18 base pairs in length, and which will selectively hybridize to *Streptomyces fradiae* DNA or mRNA encoding the SAM operon of the present invention, is provided. Preferably, the 18 or more base pair compound is DNA. These probes and primers can be prepared by enzymatic methods well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1 or suitable region therof. Plasmid pRBD26 is an especially preferred DNA vector of the present invention.

The skilled artisan understands that choosing the most appropriate cloning vector or expression vector depends upon a number of factors including the availability of restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance and metabolic markers of one type and another), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of the operably-linked genes of the present invention. The skilled artisan will recognize a number of inducible promoters which respond to a variety of inducers, for example, carbon source, metal ions, heat, and others. The practitioner also understands that the amount of nucleic acid or protein to be produced dictates, in part, the selection of the expression system. The addition of certain nucleotide sequences is useful for directing the localization of a recombinant protein. For example, a sequence encoding a signal peptide preceding the coding region of a gene, is useful for directing extra-cellular export of the resulting polypeptide.

Host cells harboring the nucleic acids disclosed herein are also provided by the present invention. A preferred host is *E. coli* which has been transfected or transformed with a vector which comprises a nucleic acid of the present invention. Another preferred host is any member of the Actinomycetes.

The present invention also provides a method for constructing a recombinant host cell capable of expressing SEQ ID NO:2, SEQ ID NO.3, and/or SEQ ID NO.5, said method comprising transforming or otherwise introducing into a host cell a recombinant DNA vector that comprises an isolated DNA sequence which encodes said SEQs or fragments thereof. Preferred vectors for expression are those which comprise SEQ ID NO:1. An especially preferred expression vector for use in *E. coli* is pRBD26, which comprises SEQ ID NO:1. (See FIG. 1). Transformed host cells may be cultured under conditions well known to skilled artisans such that the vector-encoded SAM operon enzymes are expressed in the recombinant host cell.

Regulating Production of Tylosin and Other Methylated Compounds

The SAM operon maps within the tylosin biosynthetic gene cluster, a region of the *S. fradiae* chromosome that encodes the structural and regulatory genes needed for tylosin biosynthesis. The SAM operon enzymes comprise the so-called "activated methyl cycle." This series of enzymatic reactions produces the methyl group donor molecule, SAM. The enzymatic activities encoded by the SAM operon as well as the chromosomal location of the SAM operon suggests that the SAM operon may participate in the regulation of tylosin synthesis within the cell. Thus, controlling the expression of the SAM operon genes may lead to controlled expression and production of certain methylated compounds within the cell, such as tylosin or other methylated antibiotic. Altering the levels of production of methylated compounds might be possible by altering the copy number and/or expression of the SAM operon genes.

The following examples more fully describe the present invention. Those skilled in the art will recognize that the particular reagents, equipment, and procedures described below are merely illustrative and are not intended to limit the present invention in any manner.

EXAMPLE 1

Construction of a DNA Vector Carrying the Streptomyces fradiae SAM Operon Genes

Plasmid pRBD26 (See FIG. 1) is an approximately 10.3 kilobase pair vector which can be propagated in E. coli and used for targeted integration of the SAM operon into the S. fradiae chromosome. This plasmid contains an origin of replication (OriT), an ampicillin resistance gene (Amp), the intØC31 site, useful for targeting integration into the bacteriophage ØC31 attachment site on the S. fradiae chromosome.

Plasmid pRBD26 carries a 4.8 kilobase pair fragment of S. fradiae genomic DNA (SEQ ID NO.1) that encodes the SAM operon. The S. fradiae genomic DNA was ligated into the blunt-ended EcoRV site of pSET152 (Bierman et al. Gene, 116, 43–49, 1992) using standard cloning methods. The resulting plasmid was designated pRBD26.

EXAMPLE 2

Construction of a Vector for Expressing the Streptomyces fradiae SAM Synthetase Gene in a Heterologous Host The DNA sequence coding for S. fradiae SAM synthetase is isolated from S. fradiae genomic DNA or from pRBD26, most conveniently by PCR using oligonucleotide primers complementary to the 5' and 3' terminal regions of the gene (viz. nucleotide residues 986 through 2209 of SEQ ID NO.1). For ease of cloning the SAM synthetase gene, the oligonucleotide primers are synthesized to contain one or more restriction enzyme cloning sites. Also for convenience in purifying the encoded SAM synthetase protein, the SAM synthetase gene is modified at the 5' end (viz. amino terminus of encoded protein) by adding an oligonucleotide encoding 8 histidine residues and a factor Xa cleavage site after the ATG start codon at nucleotide positions 988 of SEQ ID NO: 1. Placement of the histidine residues at the amino terminus of the encoded SAM synthetase protein enables the IMAC one-step protein purification procedure (See below).

The PCR amplified SAM synthetase gene is then inserted into an appropriate expression vector in which the SAM synthetase gene is operably-linked with a high expression promoter, for example the T7 promoter or the lambda pL promoter (See e.g. U.S. Pat. No. 4,874,703, incorporated by reference). Any suitable plasmid may be used for this purpose. A particularly useful plasmid for this purpose is pET11A, which is available commercially from Novogen (Madison, Wis.).

EXAMPLE 3

Expression of SAM Synthetase Gene in Echerichia coli

A plasmid capable of expressing SAM synthetase (see e.g. Example 2) is transformed into E. coli BL21 (DE3) (hsdS gal lcIts857 ind1Sam7nin5lacUV5-T7 gene 1) using standard methods (See e.g. Sambrook et al. Supra).

EXAMPLE 4

Purification of SAM Synthetase

Transformants selected as in Example 3 are chosen at random and tested for the presence of the transforming vector by agarose gel electrophoresis using quick plasmid preparations. Id. Colonies that contain the vector are grown, processed, and the SAM synthetase, produced by the vector-bound SAM synthetase gene, purified by immobilized metal ion affinity chromatography (IMAC), essentially as described in U.S. Pat. No. 4,569,794, the entire contents of which is hereby incorporated by reference.

Briefly, the IMAC column is prepared as follows. A metal-free chelating resin (e.g. SEPHAROSE 6B IDA, Pharmacia) is washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin are saturated with colored metal ion. The column is then ready to receive a crude cellular extract prepared from a recombinant host transformed or transfected with a vector encoding the SAM synthetase of this invention.

After washing the column with a suitable buffer, pH 7.5 to remove unbound proteins and other materials, the bound protein is eluted in a buffer at pH 4.3, essentially as described in U.S. Pat. No. 4,569,794.

EXAMPLE 5

Production of S-adenosylmethionine in a Recombinant E. coli Host Cell that Overexpresses the S. fradiae SAM Synthetase Gene A recombinant vector carrying the S. fradiae SAM synthetase gene in operable linkage with a T7 promoter (see e.g. Example 2) is transformed or otherwise introduced into a suitable strain of E. coli. The recombinant cells are grown under conditions that induce gene expression from the vector-borne T7 promoter.

A crude extract is prepared from the induced culture by any suitable method and the extract contacted with an activated polysaccharide material, for example, as described in U.S. Pat. No. 4,028,183 the entire contents of which is incorporated by reference. The polysaccharide material is activated by a reagent suitable for bonding proteins, for example cyanogen bromide. This reaction is conveniently carried out in a column. A solution of ATP and methionine in a suitable buffer is passed through the column and the eluate, which is enriched in SAM, is collected. The SAM is precipitated with picrolonic acid (See e.g. Anal. Biochem. 4, 16–28, 1971).

EXAMPLE 6

Expression of the S. Fradiae SAM Operon in a Recombinant Actinomycete

Plasmid pRBD26 is transformed into E. coli BL21 as in Example 3. Transformants harboring the plasmid are used for conjugal transfer of pRBD26 to Streptomyces spp. essentially as described in Bierman et al. "Plasmid cloning vectors for the conjugal transfer of DNA from Escherichia coli to Streptomyces spp." Gene, 116, 43–49 (1992). Briefly, one ml of a frozen mycelial culture of S. fradiae was diluted into 9 ml of TS broth and grown for 18 h aerobically at 29_C. The culture was homogenized and 2 ml was transferred into 18 ml of fresh TS broth and grown for 16 h at 29_C. to obtain a late log-phase culture. This culture was homogenized and fragmented with ultrasound, and 1 ml was transferred to 9 ml TS broth. The culture was incubated aerobically at 37_C. for 3 h. The mycelium was recovered by centrifugation, washed once in TS broth and resuspended in 2 ml TS broth (recipient culture). The *E. coli* donor was grown at 37_C. overnight in TY broth plus 100 ug apramycin (Am)/ml, subcultured 1:100 and grown for 3 h at 37_C. The cells were pelleted, washed once in TS broth and resuspended in 2 ml TS broth (donor culture). Equal volumes of the donor culture and ten-fold dilutions of the recipient culture were mixed, and 100 ul were plated to AS1 (Streptomyces medium) supplemented with 10 mM $MgCl_2$. Plates were incubated at 37_C. for 16 h, and then covered with 3 ml to 4 ml of soft R2 agar containing 1.5 mg nalidixic acid and 1.5 mg of Am. Incubation at 37_C. was continued for about a week to allow outgrowth of the exconjugants.

We claim:

1. An isolated nucleic acid fragment consisting of a nucleotide sequence encoding SAM synthetase, SEQ ID NO:2.

2. An isolated nucleic acid fragment consisting of a nucleotide sequence encoding SAM synthetase protein, SEQ ID NO:2, wherein said nucleotide sequence is selected from the group consisting of:
   (a) residues 986 through 2209 of SEQ ID NO:1;
   (b) residues 986 through 2209 of SEQ ID NO:6;
   (c) a nucleotide sequence that encodes the same SAM synthetase protein as (a) or (b), but which is degenerate in accordance with the degeneracy of the genetic code; and
   (d) a nucleotide sequence fully complementary to (a), (b), or (c).

3. The isolated nucleic acid fragment of claim 2, wherein the nucleotide sequence of said fragment consists of residues 986 through 2209 of SEQ ID NO:1 or a nucleotide sequence fully complementary thereto.

4. The isolated nucleic acid fragment of claim 2, wherein the nucleotide sequence of said fragment consists of residues 986 through 2209 of SEQ ID NO:6 or a nucleotide sequence fully complementary thereto.

5. A vector comprising said isolated nucleic acid fragment of claim 2 in operable linkage to a promoter sequence.

6. A host cell containing said vector of claim 5.

7. An isolated nucleic acid fragment consisting of a nucleotide sequence encoding methyltransferase protein, SEQ ID NO:3.

8. An isolated nucleic acid fragment consisting of a nucleotide sequence encoding methyltransferase protein, SEQ ID NO:3, wherein said nucleotide sequence is selected from the group consisting of:
   (a) residues 2241 through 3341 of SEQ ID NO:1;
   (b) residues 2241 through 3341 of SEQ ID NO:6;
   (c) a nucleotide sequence that encodes the same methyltransferase protein as (a) or (b), but which is degenerate in accordance with the degeneracy of the genetic code; and
   (d) a nucleotide sequence fully complementary to (a), (b), or (c).

9. The isolated nucleic acid fragment of claim 8, wherein the nucleotide sequence of said fragment consists of residues 2241 through 3341 of SEQ ID NO:1 or a nucleotide sequence fully complementary thereto.

10. The isolated nucleic acid fragment of claim 8, wherein the nucleotide sequence of said fragment consists of residues 2241 through 3341 of SEQ ID NO:6 or a nucleotide sequence fully complementary thereto.

11. A vector comprising said isolated nucleic acid fragment of claim 8 in operable linkage to a promoter sequence.

12. A host cell containing said vector of claim 11.

13. An isolated nucleic acid fragment consisting of a nucleotide sequence encoding methylene tetrahydrofolate reductase protein, SEQ ID NO:5.

14. An isolated nucleic acid fragment consisting of a nucleotide sequence encoding methylene tetrahydrofolate reductase protein, SEQ ID NO:5, wherein said nucleotide sequence is selected from the group consisting of:
   (a) residues 3338 through 4255 of SEQ ID NO:1;
   (b) residues 3338 through 4255 of SEQ ID NO:6;
   (c) a nucleotide sequence that encodes the same methylene tetrahydrofolate reductase protein as (a) or (b), but which is degenerate in accordance with the degeneracy of the genetic code; and
   (d) a nucleotide sequence fully complementary to (a), (b), or (c).

15. The isolated nucleic acid fragment of claim 14, wherein the nucleotide sequence of said fragment consists of residues 3338 through 4255 of SEQ ID NO:1 or a nucleotide sequence fully complementary thereto.

16. The isolated nucleic acid fragment of claim 14, wherein the nucleotide sequence of said fragment consists of residues 3338 through 4255 of SEQ ID NO:6 or a nucleotide sequence fully complementary thereto.

17. A vector comprising said isolated nucleic acid fragment of claim 14 in operable linkage to a promoter sequence.

18. A host cell containing said vector of claim 17.

19. An isolated nucleic acid fragment encoding the SAM operon from *Streptomyces fradiae,* wherein said fragment is SEQ ID NO:1 or SEQ ID NO:6.

20. A vector comprising said isolated nucleic acid fragment of claim 19, wherein said fragment is SEQ ID NO:1.

21. A host cell containing said vector of claim 20.

22. A method for producing S-adenosylmethionine, comprising:

a) culturing said host cell of claim 21; and b) recovering S-adenosylmethionine.

23. A method for constructing a recombinant host cell that expresses the SAM operon from *Streptomyces fradiae* comprising transforming a host cell with the vector of claim 20.

24. The method of claim 23, wherein said host cell is an Actinomycete.

25. The method of claim 24, further comprising culturing said Actinomycete host cell, and recovering proteins having the amino acid sequences shown in SEQ ID NO:2, SEQ ID NO:3, and SEQ ID NO:5.

26. The vector of claim 20, wherein said nucleic acid fragment is operably linked to a promoter sequence.

27. A host cell containing said vector of claim 26.

28. A method for producing proteins having the amino acid sequences shown in SEQ ID NO:2, SEQ ID NO:3, and SEQ ID NO:5 in said host cell of claim 27, comprising culturing said host cell, and recovering said proteins.

29. A method for producing S-adenosylmethionine, comprising:

(a) culturing said host cell of claim 27; and (b) recovering S-adenosylmethionine.

30. An isolated nucleic acid fragment encoding the SAM operon from *Streptomyces fradiae,* wherein said fragment consists essentially of SEQ ID NO:1 or SEQ ID NO:6.

31. A vector comprising said isolated nucleic acid fragment of claim 30, wherein said fragment is SEQ ID NO:1.

32. The vector of claim 31, wherein said isolated nucleic acid fragment is operably linked to a promoter sequence.

33. A host cell containing said vector of claim 32.

34. A method for producing proteins having the amino acid sequences shown in SEQ ID NO:2, SEQ ID NO:3, and SEQ ID NO:5 in said host cell of claim 33, comprising culturing said host cell, and recovering said proteins.

35. A method for producing S-adenosylmethionine, comprising:

(a) culturing said host cell of claim 33; and (b) recovering S-adenosylmethionine.

36. A host cell containing said vector of claim 31.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 4848 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 986..2209

(ix) FEATURE:
      (A) NAME/KEY: CDS
      (B) LOCATION: 2241..3341

(xi) SEQUENCE DESCRIPTION: SEQ ID NO:1:

```
TCATGACACC TCTGGTGAGG GGGGGCAGCT CAGCTCACCC CCGATCCGGA CACGCCGGGT      60

CCGCGGGGAG TCCCGCGGCA CCGCCGCTCG TCAACGCAGC GGGGCGAGCA CATGTCTTTT     120

TCACATTTCT CCTTGGGGGG GCGAGGCCGG CGCCCGGCCG TCGCCTTTCG TGAATGCGGA     180

GGAGCCGCAT CGCGAACGCG ATGCGGCTCC GGGGAGACTT CTCGAACCCG AGAAGGAAGG     240

GGATTCGGCG ATACGGTTCC GGAATACCGC GGCTCGTCAC GAAGCCGGTT CCGGATCAGC     300

GGTGCGGCCG TTCCAGGGCA CACCACGCCT GTTCCCCGGA GCGTGACAGG ACGCTCATCC     360

GGGTGTCAAC GCACCATTCG ACGGAGGGAG TTGGGCCGCA CCGGCCGGAG GGGTCCGACC     420

AGGGGTTTCG GGCGGGATCG AGAAACACTC GAGAAGCGGC GGAAAACACC GTGCGGCTGC     480

CCGGACCCAG GCGCCACCCG TTCTTCATCG GCTCTCCAGC CGGCCTTGAG CGCCCCGGCC     540

GGCCACCACC CGCCGAAAAC CGGGACCAAG GATTCACCGG GTTCGTGACC GTATTGCGGA     600

GTGGGATCCC GGGGATGGGA TGCCGGATGG ATTTCTGAGC AGGCGTCGCC CGGCAGCCGA     660

CGGGCCGTGG CCGGAACCGG CCGGGCCGGT CGGCGGGGTG TGCGCGGTGC CGGCCGAAGG     720

CGTGGGCCGG AGCGCGGACC CGAGCGCCGT GTCAGCGCCG TGTCAGGGCT TTGGGGGCGC     780

GCCCTCACAT ACTCGACCCG CGTTCACGGA GAGGAAGGCA GGGAAGGGCC CGTCCGCACC     840

GCGACCGGTG CCGGCGCCCC CGCCCGATGC CCGGCGCCGC CCCACCGAGC CGGACGCACC     900

GGAGGTTCCC ACCGCCCGGC CGGACGCCGG CGTGCCGTTC AGCCGGTGCG CGGGCCGGCC     960

CGAGATCTCA CACCACTGGA GAGCC ATG TCA CGT CGC CTG TTC ACC TCG GAG     1012
```

-continued

|     |     |     |     |     |     |     | Met | Ser | Arg | Arg | Leu | Phe | Thr | Ser | Glu |     |
|     |     |     |     |     |     |     |     | 1   |     |     |     | 5   |     |     |     |     |

| TCC | GTG | ACC | GAG | GGC | CAC | CCC | GAC | AAG | ATC | GCC | GAC | CGG | ATC | AGC | GAC | 1060 |
| Ser | Val | Thr | Glu | Gly | His | Pro | Asp | Lys | Ile | Ala | Asp | Arg | Ile | Ser | Asp |      |
| 10  |     |     |     | 15  |     |     |     | 20  |     |     |     |     |     |     | 25  |      |

| ACC | GTC | CTC | GAT | GCC | CTG | CTC | GCC | CGG | GAC | CCG | CGG | GCC | AGG | GTC | GCC | 1108 |
| Thr | Val | Leu | Asp | Ala | Leu | Leu | Ala | Arg | Asp | Pro | Arg | Ala | Arg | Val | Ala |      |
|     |     |     | 30  |     |     |     |     | 35  |     |     |     |     | 40  |     |     |      |

| GTC | GAG | ACC | CTG | ATC | ACC | ACC | GGT | CAG | GTC | CAT | ATC | GCC | GGC | GAG | GTC | 1156 |
| Val | Glu | Thr | Leu | Ile | Thr | Thr | Gly | Gln | Val | His | Ile | Ala | Gly | Glu | Val |      |
|     |     |     |     | 45  |     |     |     |     | 50  |     |     |     | 55  |     |     |      |

| ACC | ACC | ACC | GCG | TAC | GCG | CCC | ATC | GCC | CAA | CTG | GTG | CGC | GAC | ACC | GTC | 1204 |
| Thr | Thr | Thr | Ala | Tyr | Ala | Pro | Ile | Ala | Gln | Leu | Val | Arg | Asp | Thr | Val |      |
|     |     | 60  |     |     |     |     | 65  |     |     |     |     | 70  |     |     |     |      |

| CTG | TCC | ATC | GGC | TAC | GAC | TCC | TCG | GCC | AAG | GGC | TTC | GAC | GGC | GCC | TCG | 1252 |
| Leu | Ser | Ile | Gly | Tyr | Asp | Ser | Ser | Ala | Lys | Gly | Phe | Asp | Gly | Ala | Ser |      |
|     | 75  |     |     |     |     | 80  |     |     |     |     | 85  |     |     |     |     |      |

| TGC | GGG | GTG | TCG | GTC | TCC | ATC | GGC | GCG | CAG | TCC | CCG | GAC | ATC | GCC | CGG | 1300 |
| Cys | Gly | Val | Ser | Val | Ser | Ile | Gly | Ala | Gln | Ser | Pro | Asp | Ile | Ala | Arg |      |
| 90  |     |     |     | 95  |     |     |     |     | 100 |     |     |     | 105 |     |     |      |

| GGT | GTG | GAC | ACC | GCG | TAC | GAG | CGG | CGG | GGC | GGG | GGC | ACG | GCC | CCG | GGC | 1348 |
| Gly | Val | Asp | Thr | Ala | Tyr | Glu | Arg | Arg | Gly | Gly | Gly | Thr | Ala | Pro | Gly |      |
|     |     |     |     | 110 |     |     |     |     | 115 |     |     |     | 120 |     |     |      |

| GGA | CCG | GGT | GAC | GAG | CTG | GAC | CGG | CAG | GGC | GCG | GGC | GAC | CAG | GGC | CTG | 1396 |
| Gly | Pro | Gly | Asp | Glu | Leu | Asp | Arg | Gln | Gly | Ala | Gly | Asp | Gln | Gly | Leu |      |
|     |     |     | 125 |     |     |     |     | 130 |     |     |     |     | 135 |     |     |      |

| ATG | TTC | GGC | TAC | GCC | TGC | GAC | GAG | ACC | CCC | GAG | CTG | ATG | CCG | CTG | CCG | 1444 |
| Met | Phe | Gly | Tyr | Ala | Cys | Asp | Glu | Thr | Pro | Glu | Leu | Met | Pro | Leu | Pro |      |
|     |     |     | 140 |     |     |     |     | 145 |     |     |     |     | 150 |     |     |      |

| ATC | AAC | CTG | GCG | CAC | CGG | CTC | TCC | CGG | CGG | CTG | TCG | GAG | GTG | CGG | AAG | 1492 |
| Ile | Asn | Leu | Ala | His | Arg | Leu | Ser | Arg | Arg | Leu | Ser | Glu | Val | Arg | Lys |      |
|     |     |     |     | 155 |     |     |     |     | 160 |     |     |     | 165 |     |     |      |

| AAC | GGC | ACG | ATC | CCC | TAC | CTC | CGC | CCC | GAC | GGC | AAG | ACC | CAG | GTC | ACC | 1540 |
| Asn | Gly | Thr | Ile | Pro | Tyr | Leu | Arg | Pro | Asp | Gly | Lys | Thr | Gln | Val | Thr |      |
| 170 |     |     |     |     | 175 |     |     |     |     | 180 |     |     |     |     | 185 |      |

| ATC | GAG | TAC | GAC | GGC | GAC | AAG | GCG | GTC | CGC | CTC | GAC | ACG | GTC | GTG | GTC | 1588 |
| Ile | Glu | Tyr | Asp | Gly | Asp | Lys | Ala | Val | Arg | Leu | Asp | Thr | Val | Val | Val |      |
|     |     |     |     | 190 |     |     |     |     | 195 |     |     |     | 200 |     |     |      |

| TCC | TCC | CAG | CAC | GCC | TCC | GGC | ATC | GAC | CTG | GAC | TCG | CTA | CTG | GCG | CCC | 1636 |
| Ser | Ser | Gln | His | Ala | Ser | Gly | Ile | Asp | Leu | Asp | Ser | Leu | Leu | Ala | Pro |      |
|     |     |     |     | 205 |     |     |     |     | 210 |     |     |     |     | 215 |     |      |

| GAC | ATC | CGC | CGG | CAT | GTC | GTG | GAG | CCC | GTC | CTC | GCC | GGA | CTG | GCC | GAG | 1684 |
| Asp | Ile | Arg | Arg | His | Val | Val | Glu | Pro | Val | Leu | Ala | Gly | Leu | Ala | Glu |      |
|     |     |     | 220 |     |     |     |     | 225 |     |     |     | 230 |     |     |     |      |

| GAC | GGC | ATC | AAG | CTG | GAC | ACC | GCG | GGC | TAC | CGG | CTG | CTG | GTC | AAT | CCC | 1732 |
| Asp | Gly | Ile | Lys | Leu | Asp | Thr | Ala | Gly | Tyr | Arg | Leu | Leu | Val | Asn | Pro |      |
|     | 235 |     |     |     |     | 240 |     |     |     |     | 245 |     |     |     |     |      |

| ACC | GGC | CGG | TTC | GAG | ATC | GGC | GGC | CCG | ATG | GGC | GAC | GCG | GGC | CTG | ACC | 1780 |
| Thr | Gly | Arg | Phe | Glu | Ile | Gly | Gly | Pro | Met | Gly | Asp | Ala | Gly | Leu | Thr |      |
| 250 |     |     |     |     | 255 |     |     |     |     | 260 |     |     |     |     | 265 |      |

| GGC | CGC | AAG | ATC | ATC | ATC | GAC | ACC | TAC | GGC | GGC | ATG | GCC | CGG | CAT | GGC | 1828 |
| Gly | Arg | Lys | Ile | Ile | Ile | Asp | Thr | Tyr | Gly | Gly | Met | Ala | Arg | His | Gly |      |
|     |     |     |     | 270 |     |     |     |     | 275 |     |     |     |     | 280 |     |      |

| GGC | GGT | GCC | TTC | TCC | GGC | AAG | GAC | CCG | TCC | AAG | GTG | GAC | CGT | TCG | GCG | 1876 |
| Gly | Gly | Ala | Phe | Ser | Gly | Lys | Asp | Pro | Ser | Lys | Val | Asp | Arg | Ser | Ala |      |
|     |     |     |     | 285 |     |     |     |     | 290 |     |     |     |     | 295 |     |      |

| GCG | TAC | GCA | ATG | CGC | TGG | GTG | GCC | AAG | AAC | GTC | GTG | GCG | GCG | GGG | CTG | 1924 |
| Ala | Tyr | Ala | Met | Arg | Trp | Val | Ala | Lys | Asn | Val | Val | Ala | Ala | Gly | Leu |      |
|     |     |     | 300 |     |     |     |     | 305 |     |     |     | 310 |     |     |     |      |

-continued

```
GCC TCG CGG TGT GAG GTG CAG GTC GCC TAC GCC ATC GGC AAG GCC GAG      1972
Ala Ser Arg Cys Glu Val Gln Val Ala Tyr Ala Ile Gly Lys Ala Glu
    315                 320                 325

CCG GTC GGT CTG TTC GTG GAG ACC TTC GGC ACC GCC ACC GTG GAC GTG      2020
Pro Val Gly Leu Phe Val Glu Thr Phe Gly Thr Ala Thr Val Asp Val
330                 335                 340                 345

GAG CGG ATC GAG CAG GCG ATC GGC GAG GTC TTC GAC CTC CGC CCG GCC      2068
Glu Arg Ile Glu Gln Ala Ile Gly Glu Val Phe Asp Leu Arg Pro Ala
                350                 355                 360

GCG ATC ATC CGG GAT CTG GAC CTG CTC CGC CCG ATC TAC GCC AAG ACC      2116
Ala Ile Ile Arg Asp Leu Asp Leu Leu Arg Pro Ile Tyr Ala Lys Thr
            365                 370                 375

GCC GCC TAC GGC CAC TTC GGC CGC GAA CTG CCC GAG TTC ACC TGG GAA      2164
Ala Ala Tyr Gly His Phe Gly Arg Glu Leu Pro Glu Phe Thr Trp Glu
        380                 385                 390

CGC ACC GAC CGC ACC GAG CAG CTC ATC GCC GCG GCC GGC CTC TGA          2209
Arg Thr Asp Arg Thr Glu Gln Leu Ile Ala Ala Ala Gly Leu  *
    395                 400                 405

ACCGGCCGAC GTACCCCCGA GGAGTCCTCA C GTG CGC ATC GCC GTC ACC GGT      2261
                                 Met Arg Ile Ala Val Thr Gly
                                  1                   5

TCC ATC GCC ACC GAT CAC CTC ATG GCC TTT CCC GGC CGG TTC GGG GAC      2309
Ser Ile Ala Thr Asp His Leu Met Ala Phe Pro Gly Arg Phe Gly Asp
        10                  15                  20

CAG CTG ATC CCC GAT CAG CTC GCC CGG GTC TCG CTG TCT TTC CTC GTC      2357
Gln Leu Ile Pro Asp Gln Leu Ala Arg Val Ser Leu Ser Phe Leu Val
    25                  30                  35

GAC GGG CTC GAG GTG CGC CGG GGC GGA GTG GCC GTC GGC ATC GCC TTC      2405
Asp Gly Leu Glu Val Arg Arg Gly Gly Val Ala Val Gly Ile Ala Phe
40                  45                  50                  55

GGC CTG GGC CGT CCG GGC CCC ACG CCG CTC CTC GTC GGC GCC GTG GGG      2453
Gly Leu Gly Arg Pro Gly Pro Thr Pro Leu Leu Val Gly Ala Val Gly
                60                  65                  70

AAC GAC TTC GCC GAC TAC GGG ACC TGG CCG AAG GAG CAC GGC GTC GAC      2501
Asn Asp Phe Ala Asp Tyr Gly Thr Trp Pro Lys Glu His Gly Val Asp
            75                  80                  85

ACC GGA GGC GTT CTG GTC CCG ACC GAG CAC CAG ACC GCC CGC TTC CTG      2549
Thr Gly Gly Val Leu Val Pro Thr Glu His Gln Thr Ala Arg Phe Leu
        90                  95                  100

TGC ATC ACC GAC CGG GAC GCC AAC CAG ATC GCG GCC TCC TAC ACG GGT      2597
Cys Ile Thr Asp Arg Asp Ala Asn Gln Ile Ala Ala Ser Tyr Thr Gly
    105                 110                 115

GCG ATG CGG GAG GCC CGG GAC ATC GGC CTG CGG CGG ACG GGC GCT CTG      2645
Ala Met Arg Glu Ala Arg Asp Ile Gly Leu Arg Arg Thr Gly Ala Leu
120                 125                 130                 135

CCG GCG CCC CGG CAC GGT CTG GTC CTC ATC TGC CCC GAC GAC CCG GCG      2693
Pro Ala Pro Arg His Gly Leu Val Leu Ile Cys Pro Asp Asp Pro Ala
                140                 145                 150

GCG ATG GTG CGC CAC ACC GCG CAG TGC CGG GAG CCG GGC CTG CCG TTC      2741
Ala Met Val Arg His Thr Ala Gln Cys Arg Glu Pro Gly Leu Pro Phe
            155                 160                 165

GTC GCC GAC CCC TCC CAG CAG CTC GCC CGG CTG GAG ACG GAC GAG GTA      2789
Val Ala Asp Pro Ser Gln Gln Leu Ala Arg Leu Glu Thr Asp Glu Val
        170                 175                 180

CGC GCG CTG GTG CAC GGC GCC CAC TGG GTC TTC ACC AAC GAG TAC GAG      2837
Arg Ala Leu Val His Gly Ala His Trp Val Phe Thr Asn Glu Tyr Glu
    185                 190                 195

GCC GCG CTG CTG CTC GAG CAC TCC GGC TGG AAA CAC TCC GAG ACC CTG      2885
Ala Ala Leu Leu Leu Glu His Ser Gly Trp Lys His Ser Glu Thr Leu
200                 205                 210                 215
```

```
GAA CGG GTG GGC GCC TGG GTC ACC ACG CTC GGC GGT GCC GGG GTC CGG     2933
Glu Arg Val Gly Ala Trp Val Thr Thr Leu Gly Gly Ala Gly Val Arg
            220                 225                 230
ATC GAG CGC GCG GGC GAG CCA CCG CTG ACG GTG CCC GCG GTC CCC GAT     2981
Ile Glu Arg Ala Gly Glu Pro Pro Leu Thr Val Pro Ala Val Pro Asp
            235                 240                 245
GTC CCC GTG GTC GAT CCG ACC GGG ATC GGT GCC GCC TTC CGG GCC GGT     3029
Val Pro Val Val Asp Pro Thr Gly Ile Gly Ala Ala Phe Arg Ala Gly
            250                 255                 260
TTC CTG GCC GGC GCC GGG CGC GGC CTT TCC ATC GTC TCC GCC GCC CGC     3077
Phe Leu Ala Gly Ala Gly Arg Gly Leu Ser Ile Val Ser Ala Ala Arg
265                 270                 275
CTG GGC TGC GTC CTG GCG GCG CGG GCG CTG GGG ACG GTC GGC CCC GCA     3125
Leu Gly Cys Val Leu Ala Ala Arg Ala Leu Gly Thr Val Gly Pro Ala
280                 285                 290                 295
GAC CTA CCG GAC CGA TCC GGC GGA TCC GCT CGC CAC GGC GAG GGA CGC     3173
Asp Leu Pro Asp Arg Ser Gly Gly Ser Ala Arg His Gly Glu Gly Arg
            300                 305                 310
GTA CGG CGC GGA CGC GGC GGC GCG GCT CGC CCT CGG GCT GGG CGG CCG     3221
Val Arg Arg Gly Arg Gly Gly Ala Ala Arg Pro Arg Ala Gly Arg Pro
            315                 320                 325
CAC ATG ACC CGG CCC TGT CCC GGC TCC CGG CGC GAG CCA CCG GCC GGA     3269
His Met Thr Arg Pro Cys Pro Gly Ser Arg Arg Glu Pro Pro Ala Gly
            330                 335                 340
CGC CCG GCA CGG GCC GCC GCC GTC ATC CGC CGC CCC GGC GCC GGC GGG     3317
Arg Pro Ala Arg Ala Ala Ala Val Ile Arg Arg Pro Gly Ala Gly Gly
            345                 350                 355
CCG ACC GCG GGA GGC TGC CGG TGA GGACCACCCT GCGCGAGATC CTCGGCAGCG    3371
Pro Thr Ala Gly Gly Cys Arg *
360                 365

GCCGGCTCTC CTTCTCCCAC GAGTTCTTCC CCCCGAGGAC GGAGGCCGGC ACGCGGACGC    3431
TCTGGAACGC GATCCGCCGG ATCGAACCGC TGGCCCCGAC CTTCGTCTCG GTCACCTACG    3491
GCGCCGGCGG CTCCTCCCGG GACCGCACCG TCGAGGTCAC CAAGCGCATC GCCACCGACA    3551
CCACCCTGCG GCCGGTCGCC CATCTCACCG CCGTCGGCCA CTCCGTCGCC GAACTGCGCC    3611
GCATCATCGG CCAGTACGCG GACGCCGGTG TCCGGGACGT ACTCGCCCTG CGCGGCGACC    3671
CGCCGGGGGA TCCGAACGCG CCCTGGGTCC CGCATCCCGA GGGGCTCACC CACGCCCATG    3731
AACTCGTCTC GCTGGTGCGC GGATCGGGCG GCTTCGGTGT GGGCGTCGCG GCCTTCCCCG    3791
AGCGTCATCC CCGTTCCCCC GACTGGGACA GCGAGATCCG GCACTTCGTG CGCAAGTGCC    3851
GGGCCGGCGC CGACTACGCC ATCACGCAGA TGTTCTTCCG GGTCGAGGAC TATCTGCGGC    3911
TGCGGGACCG GGTCGCGGCC GCCGGCTGCT GCACCCCGGT CATCCCCGGG ATCATGCCCG    3971
CCACCGACGT GCGGCAGATC GCGCGCTTCG CCGAGCTTTC CCACGCCACC TTCCCCGAAG    4031
GTCTCGCGCG GCGGCTGGAG GCCGCCCGCG GCAACCCGGC CGAGGGACAC CGCATCGGGG    4091
TCGAGTACGC CACCGCCATG GCCGGCCGGC TGCTCGCCGA AGGCGCCCCG GGACTGCACT    4151
ACATCACTCT CAACCGCTCC ACCGCGACGT TGGAGATCCA CCGGAACATC CTGGGCACAC    4211
CAGCCCCGGG GAGTGCCCGG CAGGTCCTCG CGGCTCCCCT CTGACCGGCG GGACCTCTC     4271
GGCCCGGCCC GCACGGCGGC GGGCCCCGGC TGCGCTCCCC CGGGTCGGGT CCGGCCCGCC    4331
GTCCCGGCCG CCGTCCGGGC CGGCGGCGGC GGACCGTGCG CGGGCGAAGC ACACCGCCGC    4391
GCGTTTCCCC CGGGTCCCGG CGCCGCGGGC GGCCCCGGCG CCGGAACCCG GCCGTCCGCT    4451
CGCCGCGCCC CCCCGGGGGG GGACGGCCGG ACGGCCCTCT TCCGGGACGG CACTCAGCGT    4511
```

```
CCGCCGGAGA CGACGCCCTC GCGCAGCTCC AGATGCGAGC CGGTGAACCG GCTTCGCATC    4571

CGCCGGTCGT GGGTGACCAG CACCAGCGCG CCCCCGTAGC CCGTCAGCGC CTCCTCCAAC    4631

TCCTCCACCA GCGCCGGTGA GAGGTGGTTG GTGGGCTCGT CCAGCAGGAG CAGACCCACC    4691

GGCTCGCTGA CCAGCCGGGC CAGTTCGATG CGGCGGCGCT GACCGTACGA CAGCTCCCCG    4751

ACCCGCAGCC GCAGCGCCTC CGGCTCGAAC AGGCCGAGGG ACAGCAGCCG GTCGGCCTGT    4811

TCGTCCCGGT CGCCGGGCCG GTTGTGGGCG AAGGCCT                              4848
```

(2) INFORMATION FOR SEQ ID NO:2:

(i) SEQUENCE CHARACTERISTICS:
        (A) LENGTH: 407 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Arg Arg Leu Phe Thr Ser Glu Ser Val Thr Glu Gly His Pro
 1               5                  10                  15

Asp Lys Ile Ala Asp Arg Ile Ser Asp Thr Val Leu Asp Ala Leu Leu
            20                  25                  30

Ala Arg Asp Pro Arg Ala Arg Val Ala Val Glu Thr Leu Ile Thr Thr
        35                  40                  45

Gly Gln Val His Ile Ala Gly Glu Val Thr Thr Thr Ala Tyr Ala Pro
    50                  55                  60

Ile Ala Gln Leu Val Arg Asp Thr Val Leu Ser Ile Gly Tyr Asp Ser
65                  70                  75                  80

Ser Ala Lys Gly Phe Asp Gly Ala Ser Cys Gly Val Ser Val Ser Ile
                85                  90                  95

Gly Ala Gln Ser Pro Asp Ile Ala Arg Gly Val Asp Thr Ala Tyr Glu
            100                 105                 110

Arg Arg Gly Gly Gly Thr Ala Pro Gly Gly Pro Gly Asp Glu Leu Asp
        115                 120                 125

Arg Gln Gly Ala Gly Asp Gln Gly Leu Met Phe Gly Tyr Ala Cys Asp
    130                 135                 140

Glu Thr Pro Glu Leu Met Pro Leu Pro Ile Asn Leu Ala His Arg Leu
145                 150                 155                 160

Ser Arg Arg Leu Ser Glu Val Arg Lys Asn Gly Thr Ile Pro Tyr Leu
                165                 170                 175

Arg Pro Asp Gly Lys Thr Gln Val Thr Ile Glu Tyr Asp Gly Asp Lys
            180                 185                 190

Ala Val Arg Leu Asp Thr Val Val Ser Ser Gln His Ala Ser Gly
        195                 200                 205

Ile Asp Leu Asp Ser Leu Leu Ala Pro Asp Ile Arg Arg His Val Val
    210                 215                 220

Glu Pro Val Leu Ala Gly Leu Ala Glu Asp Gly Ile Lys Leu Asp Thr
225                 230                 235                 240

Ala Gly Tyr Arg Leu Leu Val Asn Pro Thr Gly Arg Phe Glu Ile Gly
                245                 250                 255

Gly Pro Met Gly Asp Ala Gly Leu Thr Gly Arg Lys Ile Ile Ile Asp
            260                 265                 270

Thr Tyr Gly Gly Met Ala Arg His Gly Gly Gly Ala Phe Ser Gly Lys
        275                 280                 285

Asp Pro Ser Lys Val Asp Arg Ser Ala Ala Tyr Ala Met Arg Trp Val
```

```
                 290                     295                     300
Ala Lys Asn Val Val Ala Gly Leu Ala Ser Arg Cys Glu Val Gln
305                     310                     315                     320

Val Ala Tyr Ala Ile Gly Lys Ala Glu Pro Val Gly Leu Phe Val Glu
                    325                     330                     335

Thr Phe Gly Thr Ala Thr Val Asp Val Glu Arg Ile Glu Gln Ala Ile
                    340                     345                     350

Gly Glu Val Phe Asp Leu Arg Pro Ala Ala Ile Ile Arg Asp Leu Asp
                    355                     360                     365

Leu Leu Arg Pro Ile Tyr Ala Lys Thr Ala Ala Tyr Gly His Phe Gly
370                     375                     380

Arg Glu Leu Pro Glu Phe Thr Trp Glu Arg Thr Asp Arg Thr Glu Gln
385                     390                     395                     400

Leu Ile Ala Ala Gly Leu
                    405

(2) INFORMATION FOR SEQ ID NO:3:

(i) SEQUENCE CHARACTERISTICS:
        (A) LENGTH: 366 amino acids
        (B) TYPE: amino acid
        (D) TOPOLOGY: linear (ii) MOLECULE TYPE: protein (xi) SEQUENCE DESCRIPTION: SEQ ID NO:3:

Met Arg Ile Ala Val Thr Gly Ser Ile Ala Thr Asp His Leu Met Ala
1                   5                   10                  15

Phe Pro Gly Arg Phe Gly Asp Gln Leu Ile Pro Asp Gln Leu Ala Arg
                    20                  25                  30

Val Ser Leu Ser Phe Leu Val Asp Gly Leu Glu Val Arg Arg Gly Gly
                35                  40                  45

Val Ala Val Gly Ile Ala Phe Gly Leu Gly Arg Pro Gly Pro Thr Pro
            50                  55                  60

Leu Leu Val Gly Ala Val Gly Asn Asp Phe Ala Asp Tyr Gly Thr Trp
65                  70                  75                  80

Pro Lys Glu His Gly Val Asp Thr Gly Gly Val Leu Val Pro Thr Glu
                85                  90                  95

His Gln Thr Ala Arg Phe Leu Cys Ile Thr Asp Arg Asp Ala Asn Gln
                100                 105                 110

Ile Ala Ala Ser Tyr Thr Gly Ala Met Arg Glu Ala Arg Asp Ile Gly
            115                 120                 125

Leu Arg Arg Thr Gly Ala Leu Pro Ala Pro Arg His Gly Leu Val Leu
130                 135                 140

Ile Cys Pro Asp Asp Pro Ala Ala Met Val Arg His Thr Ala Gln Cys
145                 150                 155                 160

Arg Glu Pro Gly Leu Pro Phe Val Ala Asp Pro Ser Gln Gln Leu Ala
                165                 170                 175

Arg Leu Glu Thr Asp Glu Val Arg Ala Leu Val His Gly Ala His Trp
            180                 185                 190

Val Phe Thr Asn Glu Tyr Glu Ala Ala Leu Leu Leu Glu His Ser Gly
        195                 200                 205

Trp Lys His Ser Glu Thr Leu Glu Arg Val Gly Ala Trp Val Thr Thr
    210                 215                 220

Leu Gly Gly Ala Gly Val Arg Ile Glu Arg Ala Gly Glu Pro Pro Leu
225                 230                 235                 240
```

```
Thr Val Pro Ala Val Pro Asp Val Pro Val Val Asp Pro Thr Gly Ile
                245                 250                 255

Gly Ala Ala Phe Arg Ala Gly Phe Leu Ala Gly Ala Gly Arg Gly Leu
                260                 265                 270

Ser Ile Val Ser Ala Ala Arg Leu Gly Cys Val Leu Ala Ala Arg Ala
                275                 280                 285

Leu Gly Thr Val Gly Pro Ala Asp Leu Pro Asp Arg Ser Gly Gly Ser
            290                 295                 300

Ala Arg His Gly Glu Gly Arg Val Arg Arg Gly Arg Gly Gly Ala Ala
305                 310                 315                 320

Arg Pro Arg Ala Gly Arg Pro His Met Thr Arg Pro Cys Pro Gly Ser
                325                 330                 335

Arg Arg Glu Pro Pro Ala Gly Arg Pro Ala Arg Ala Ala Ala Val Ile
                340                 345                 350

Arg Arg Pro Gly Ala Gly Gly Pro Thr Ala Gly Gly Cys Arg
            355                 360                 365

(2) INFORMATION FOR SEQ ID NO:4:

(i) SEQUENCE CHARACTERISTICS:
        (A) LENGTH: 4848 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 3338..4255

(xi) SEQUENCE DESCRIPTION: SEQ ID NO:4:
```

| | | | | | |
|---|---|---|---|---|---|
| TCATGACACC | TCTGGTGAGG | GGGGGCAGCT | CAGCTCACCC | CCGATCCGGA | CACGCCGGGT | 60 |
| CCGCGGGGAG | TCCCGCGGCA | CCGCCGCTCG | TCAACGCAGC | GGGGCGAGCA | CATGTCTTTT | 120 |
| TCACATTTCT | CCTTGGGGGG | GCGAGGCCGG | CGCCCGGCCG | TCGCCTTTCG | TGAATGCGGA | 180 |
| GGAGCCGCAT | CGCGAACGCG | ATGCGGCTCC | GGGGAGACTT | CTCGAACCCG | AGAAGGAAGG | 240 |
| GGATTCGGCG | ATACGGTTCC | GGAATACCGC | GGCTCGTCAC | GAAGCCGGTT | CCGGATCAGC | 300 |
| GGTGCGGCCG | TTCCAGGGCA | CACCACGCCT | GTTCCCCGGA | GCGTGACAGG | ACGCTCATCC | 360 |
| GGGTGTCAAC | GCACCATTCG | ACGGAGGGAG | TTGGGCCGCA | CCGGCCGGAG | GGGTCCGACC | 420 |
| AGGGGTTTCG | GGCGGGATCG | AGAAACACTC | GAGAAGCGGC | GGAAAACACC | GTGCGGCTGC | 480 |
| CCGGACCCAG | GCGCCACCCG | TTCTTCATCG | GCTCTCCAGC | CGGCCTTGAG | CGCCCCGGCC | 540 |
| GGCCACCACC | CGCCGAAAAC | CGGGACCAAG | GATTCACCGG | GTTCGTGACC | GTATTGCGGA | 600 |
| GTGGATCCC | GGGGATGGGA | TGCCGGATGG | ATTTCTGAGC | AGGCGTCGCC | CGGCAGCCGA | 660 |
| CGGGCCGTGG | CCGGAACCGG | CCGGGCCGGT | CGGCGGGGTG | TGCGCGGTGC | CGGCCGAAGG | 720 |
| CGTGGGCCGG | AGCGCGGACC | CGAGCGCCGT | GTCAGCGCCG | TGTCAGGGCT | TTGGGGGCGC | 780 |
| GCCCTCACAT | ACTCGACCCG | CGTTCACGGA | GAGGAAGGCA | GGGAAGGGCC | CGTCCGCACC | 840 |
| GCGACCGGTG | CCGGCGCCCC | CGCCCGATGC | CCGGCGCCGC | CCCACCGAGC | CGGACGCACC | 900 |
| GGAGGTTCCC | ACCGCCCGGC | CGGACGCCGG | CGTGCCGTTC | AGCCGGTGCG | CGGGCCGGCC | 960 |
| CGAGATCTCA | CACCACTGGA | GAGCCATGTC | ACGTCGCCTG | TTCACCTCGG | AGTCCGTGAC | 1020 |

```
CGAGGGCCAC CCCGACAAGA TCGCCGACCG GATCAGCGAC ACCGTCCTCG ATGCCCTGCT    1080

CGCCCGGGAC CCGCGGGCCA GGGTCGCCGT CGAGACCCTG ATCACCACCG GTCAGGTCCA    1140

TATCGCCGGC GAGGTCACCA CCACCGCGTA CGCGCCCATC GCCCAACTGG TGCGCGACAC    1200

CGTCCTGTCC ATCGGCTACG ACTCCTCGGC CAAGGGCTTC GACGGCGCCT CGTGCGGGGT    1260

GTCGGTCTCC ATCGGCGCGC AGTCCCCGGA CATCGCCCGG GGTGTGGACA CCGCGTACGA    1320

GCGGCGGGGC GGGGGCACGG CCCCGGGCGG ACCGGGTGAC GAGCTGGACC GGCAGGGCGC    1380

GGGCGACCAG GGCCTGATGT TCGGCTACGC CTGCGACGAG ACCCCCGAGC TGATGCCGCT    1440

GCCGATCAAC CTGGCGCACC GGCTCTCCCG GCGGCTGTCG GAGGTGCGGA AGAACGGCAC    1500

GATCCCCTAC CTCCGCCCCG ACGGCAAGAC CCAGGTCACC ATCGAGTACG ACGGCGACAA    1560

GGCGGTCCGC CTCGACACGG TCGTGGTCTC CTCCCAGCAC GCCTCCGGCA TCGACCTGGA    1620

CTCGCTACTG GCGCCCGACA TCCGCCGGCA TGTCGTGGAG CCCGTCCTCG CCGGACTGGC    1680

CGAGGACGGC ATCAAGCTGG ACACCGCGGG CTACCGGCTG CTGGTCAATC CCACCGGCCG    1740

GTTCGAGATC GGCGGCCCGA TGGGCGACGC GGGCCTGACC GGCCGCAAGA TCATCATCGA    1800

CACCTACGGC GGCATGGCCC GGCATGGCGG CGGTGCCTTC TCCGGCAAGG ACCCGTCCAA    1860

GGTGGACCGT TCGGCGGCGT ACGCAATGCG CTGGGTGGCC AAGAACGTCG TGGCGGCGGG    1920

GCTGGCCTCG CGGTGTGAGG TGCAGGTCGC CTACGCCATC GGCAAGGCCG AGCCGGTCGG    1980

TCTGTTCGTG GAGACCTTCG GCACCGCCAC CGTGGACGTG GAGCGGATCG AGCAGGCGAT    2040

CGGCGAGGTC TTCGACCTCC GCCCGGCCGC GATCATCCGG GATCTGGACC TGCTCCGCCC    2100

GATCTACGCC AAGACCGCCG CCTACGGCCA CTTCGGCCGC GAACTGCCCG AGTTCACCTG    2160

GGAACGCACC GACCGCACCG AGCAGCTCAT CGCCGCGGCC GGCCTCTGAA CCGGCCGACG    2220

TACCCCCGAG GAGTCCTCAC GTGCGCATCG CCGTCACCGG TTCCATCGCC ACCGATCACC    2280

TCATGGCCTT TCCCGGCCGG TTCGGGGACC AGCTGATCCC CGATCAGCTC GCCCGGGTCT    2340

CGCTGTCTTT CCTCGTCGAC GGGCTCGAGG TGCGCCGGGG CGGAGTGGCC GTCGGCATCG    2400

CCTTCGGCCT GGGCCGTCCG GGCCCCACGC CGCTGCTCGT CGGCGCCGTG GGGAACGACT    2460

TCGCCGACTA CGGGACCTGG CCGAAGGAGC ACGGCGTCGA CACCGGAGGC GTTCTGGTCC    2520

CGACCGAGCA CCAGACCGCC CGCTTCCTGT GCATCACCGA CCGGGACGCC AACCAGATCG    2580

CGGCCTCCTA CACGGGTGCG ATGCGGGAGG CCCGGGACAT CGGCCTGCGG CGGACGGGCG    2640

CTCTGCCGGC GCCCCGGCAC GGTCTGGTCC TCATCTGCCC CGACGACCCG GCGGCGATGG    2700

TGCGCCACAC CGCGCAGTGC CGGGAGCCGG GCCTGCCGTT CGTCGCCGAC CCCTCCCAGC    2760

AGCTCGCCCG GCTGGAGACG GACGAGGTAC GCGCGCTGGT GCACGGCGCC CACTGGGTCT    2820

TCACCAACGA GTACGAGGCC GCGCTGCTGC TCGAGCACTC CGGCTGGAAA CACTCCGAGA    2880

CCCTGGAACG GGTGGGCGCC TGGGTCACCA CGCTCGGCGG TGCCGGGGTC CGGATCGAGC    2940

GCGCGGGCGA GCCACCGCTG ACGGTGCCCG CGGTCCCCGA TGTCCCCGTG GTCGATCCGA    3000

CCGGGATCGG TGCCGCCTTC CGGGCCGGTT TCCTGGCCGG CGCGGGCGC GGCCTTTCCA    3060

TCGTCTCCGC CGCCCGCCTG GGCTGCGTCC TGGCGGCGCG GCGCTGGGG ACGGTCGGCC    3120

CCGCAGACCT ACCGGACCGA TCCGGCGGAT CCGCTCGCCA CGGCGAGGGA CGCGTACGGC    3180

GCGGACGCGG CGGCGCGGCT CGCCCTCGGG CTGGGCGGCC GCACATGACC CGGCCCTGTC    3240

CCGGCTCCCG GCGCGAGCCA CCGGCCGGAC GCCCGGCACG GCCGCCGCC GTCATCCGCC    3300

GCCCCGGCGC CGGCGGGCCG ACCGCGGGAG GCTGCCG GTG AGG ACC ACC CTG CGC    3355
                                         Met Arg Thr Thr Leu Arg
```

```
                                    1               5
GAG ATC CTC GGC AGC GGC CGG CTC TCC TTC TCC CAC GAG TTC TTC CCC     3403
Glu Ile Leu Gly Ser Gly Arg Leu Ser Phe Ser His Glu Phe Phe Pro
             10              15              20

CCG AGG ACG GAG GCC GGC ACG CGG ACG CTC TGG AAC GCG ATC CGC CGG     3451
Pro Arg Thr Glu Ala Gly Thr Arg Thr Leu Trp Asn Ala Ile Arg Arg
         25              30              35

ATC GAA CCG CTG GCC CCG ACC TTC GTC TCG GTC ACC TAC GGC GCC GGC     3499
Ile Glu Pro Leu Ala Pro Thr Phe Val Ser Val Thr Tyr Gly Ala Gly
         40              45              50

GGC TCC TCC CGG GAC CGC ACC GTC GAG GTC ACC AAG CGC ATC GCC ACC     3547
Gly Ser Ser Arg Asp Arg Thr Val Glu Val Thr Lys Arg Ile Ala Thr
55              60              65              70

GAC ACC ACC CTG CGG CCG GTC GCC CAT CTC ACC GCC GTC GGC CAC TCC     3595
Asp Thr Thr Leu Arg Pro Val Ala His Leu Thr Ala Val Gly His Ser
             75              80              85

GTC GCC GAA CTG CGC CGC ATC ATC GGC CAG TAC GCG GAC GCC GGT GTC     3643
Val Ala Glu Leu Arg Arg Ile Ile Gly Gln Tyr Ala Asp Ala Gly Val
         90              95             100

CGG GAC GTA CTC GCC CTG CGC GGC GAC CCG CCG GGG GAT CCG AAC GCG     3691
Arg Asp Val Leu Ala Leu Arg Gly Asp Pro Pro Gly Asp Pro Asn Ala
         105             110             115

CCC TGG GTC CCG CAT CCC GAG GGG CTC ACC CAC GCC CAT GAA CTC GTC     3739
Pro Trp Val Pro His Pro Glu Gly Leu Thr His Ala His Glu Leu Val
         120             125             130

TCG CTG GTG CGC GGA TCG GGC GGC TTC GGT GTG GGC GTC GCG GCC TTC     3787
Ser Leu Val Arg Gly Ser Gly Gly Phe Gly Val Gly Val Ala Ala Phe
135             140             145             150

CCC GAG CGT CAT CCC CGT TCC CCC GAC TGG GAC AGC GAG ATC CGG CAC     3835
Pro Glu Arg His Pro Arg Ser Pro Asp Trp Asp Ser Glu Ile Arg His
             155             160             165

TTC GTG CGC AAG TGC CGG GCC GGC GCC GAC TAC GCC ATC ACG CAG ATG     3883
Phe Val Arg Lys Cys Arg Ala Gly Ala Asp Tyr Ala Ile Thr Gln Met
         170             175             180

TTC TTC CGG GTC GAG GAC TAT CTG CGG CTG CGG GAC CGG GTC GCG GCC     3931
Phe Phe Arg Val Glu Asp Tyr Leu Arg Leu Arg Asp Arg Val Ala Ala
         185             190             195

GCC GGC TGC TGC ACC CCG GTC ATC CCC GGG ATC ATG CCC GCC ACC GAC     3979
Ala Gly Cys Cys Thr Pro Val Ile Pro Gly Ile Met Pro Ala Thr Asp
         200             205             210

GTG CGG CAG ATC GCG CGC TTC GCC GAG CTT TCC CAC GCC ACC TTC CCC     4027
Val Arg Gln Ile Ala Arg Phe Ala Glu Leu Ser His Ala Thr Phe Pro
215             220             225             230

GAA GGT CTC GCG CGG CGG CTG GAG GCC GCC CGC GGC AAC CCG GCC GAG     4075
Glu Gly Leu Ala Arg Arg Leu Glu Ala Ala Arg Gly Asn Pro Ala Glu
             235             240             245

GGA CAC CGC ATC GGG GTC GAG TAC GCC ACC GCC ATG GCC GGC CGG CTG     4123
Gly His Arg Ile Gly Val Glu Tyr Ala Thr Ala Met Ala Gly Arg Leu
         250             255             260

CTC GCC GAA GGC GCC CCG GGA CTG CAC TAC ATC ACT CTC AAC CGC TCC     4171
Leu Ala Glu Gly Ala Pro Gly Leu His Tyr Ile Thr Leu Asn Arg Ser
         265             270             275

ACC GCG ACG TTG GAG ATC CAC CGG AAC ATC CTG GGC ACA CCA GCC CCG     4219
Thr Ala Thr Leu Glu Ile His Arg Asn Ile Leu Gly Thr Pro Ala Pro
         280             285             290

GGG AGT GCC CGG CAG GTC CTC GCG GCT CCC CTC TGA CCGGCGGGGA          4265
Gly Ser Ala Arg Gln Val Leu Ala Ala Pro Leu  *
295             300             305

CCTCTCGGCC CGGCCCGCAC GGCGGCGGGC CCCGGCTGCG CTCCCCCGGG TCGGGTCCGG   4325
```

-continued

```
CCCGCCGTCC CGGCCGCCGT CCGGGCCGGC GGCGGCGGAC CGTGCGCGGG CGAAGCACAC    4385

CGCCGCGCGT TTCCCCCGGG TCCCGGCGCC GCGGGCGGCC CCGGCGCCGG AACCCGGCCG    4445

TCCGCTCGCC GCGCCCCCCC GGGGGGGGAC GGCCGGACGG CCCTCTTCCG GGACGGCACT    4505

CAGCGTCCGC CGGAGACGAC GCCCTCGCGC AGCTCCAGAT GCGAGCCGGT GAACCGGCTT    4565

CGCATCCGCC GGTCGTGGGT GACCAGCACC AGCGCGCCCC CGTAGCCCGT CAGCGCCTCC    4625

TCCAACTCCT CCACCAGCGC CGGTGAGAGG TGGTTGGTGG GCTCGTCCAG CAGGAGCAGA    4685

CCCACCGGCT CGCTGACCAG CCGGGCCAGT TCGATGCGGG GGCGCTGACC GTACGACAGC    4745

TCCCCGACCC GCAGCCGCAG CGCCTCCGGC TCGAACAGGC CGAGGGACAG CAGCCGGTCG    4805

GCCTGTTCGT CCCGGTCGCC GGGCCGGTTG TGGGCGAAGG CCT                      4848
```

(2) INFORMATION FOR SEQ ID NO:5:

(i) SEQUENCE CHARACTERISTICS:
        (A) LENGTH: 305 amino acids
        (B) TYPE: amino acid
        (D) TOPOLOGY: linear (ii) MOLECULE TYPE: protein (xi) SEQUENCE DESCRIPTION: SEQ ID NO:5:

```
Met Arg Thr Thr Leu Arg Glu Ile Leu Gly Ser Gly Arg Leu Ser Phe
 1               5                  10                  15

Ser His Glu Phe Phe Pro Pro Arg Thr Glu Ala Gly Thr Arg Thr Leu
            20                  25                  30

Trp Asn Ala Ile Arg Arg Ile Glu Pro Leu Ala Pro Thr Phe Val Ser
        35                  40                  45

Val Thr Tyr Gly Ala Gly Gly Ser Ser Arg Asp Arg Thr Val Glu Val
    50                  55                  60

Thr Lys Arg Ile Ala Thr Asp Thr Thr Leu Arg Pro Val Ala His Leu
65                  70                  75                  80

Thr Ala Val Gly His Ser Val Ala Glu Leu Arg Arg Ile Ile Gly Gln
                85                  90                  95

Tyr Ala Asp Ala Gly Val Arg Asp Val Leu Ala Leu Arg Gly Asp Pro
            100                 105                 110

Pro Gly Asp Pro Asn Ala Pro Trp Val Pro His Pro Glu Gly Leu Thr
        115                 120                 125

His Ala His Glu Leu Val Ser Leu Val Arg Gly Ser Gly Gly Phe Gly
    130                 135                 140

Val Gly Val Ala Ala Phe Pro Glu Arg His Pro Arg Ser Pro Asp Trp
145                 150                 155                 160

Asp Ser Glu Ile Arg His Phe Val Arg Lys Cys Arg Ala Gly Ala Asp
                165                 170                 175

Tyr Ala Ile Thr Gln Met Phe Phe Arg Val Glu Asp Tyr Leu Arg Leu
            180                 185                 190

Arg Asp Arg Val Ala Ala Ala Gly Cys Cys Thr Pro Val Ile Pro Gly
        195                 200                 205

Ile Met Pro Ala Thr Asp Val Arg Gln Ile Ala Arg Phe Ala Glu Leu
    210                 215                 220

Ser His Ala Thr Phe Pro Glu Gly Leu Ala Arg Arg Leu Glu Ala Ala
225                 230                 235                 240

Arg Gly Asn Pro Ala Glu Gly His Arg Ile Gly Val Glu Tyr Ala Thr
                245                 250                 255
```

```
Ala Met Ala Gly Arg Leu Leu Ala Glu Gly Ala Pro Gly Leu His Tyr
            260                 265                 270

Ile Thr Leu Asn Arg Ser Thr Ala Thr Leu Glu Ile His Arg Asn Ile
        275                 280                 285

Leu Gly Thr Pro Ala Pro Gly Ser Ala Arg Gln Val Leu Ala Ala Pro
    290                 295                 300

Leu
305

(2) INFORMATION FOR SEQ ID NO:6:

(i) SEQUENCE CHARACTERISTICS:
        (A) LENGTH: 4848 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:6:
```

| | | | | | |
|---|---|---|---|---|---|
| UCAUGACACC | UCUGGUGAGG | GGGGGCAGCU | CAGCUCACCC | CCGAUCCGGA | CACGCCGGGU | 60 |
| CCGCGGGGAG | UCCCGCGGCA | CCGCCGCUCG | UCAACGCAGC | GGGGCGAGCA | CAUGUCUUUU | 120 |
| UCACAUUUCU | CCUUGGGGGG | GCGAGGCCGG | CGCCCGGCCG | UCGCCUUUCG | UGAAUGCGGA | 180 |
| GGAGCCGCAU | CGCGAACGCG | AUGCGGCUCC | GGGGAGACUU | CUCGAACCCG | AGAAGGAAGG | 240 |
| GGAUUCGGCG | AUACGGUUCC | GGAAUACCGC | GGCUCGUCAC | GAAGCCGGUU | CCGGAUCAGC | 300 |
| GGUGCGGCCG | UUCCAGGGCA | CACCACGCCU | GUUCCCCGGA | GCGUGACAGG | ACGCUCAUCC | 360 |
| GGGUGUCAAC | GCACCAUUCG | ACGGAGGGAG | UUGGGCCGCA | CCGGCCGGAG | GGGUCCGACC | 420 |
| AGGGGUUUCG | GGCGGGAUCG | AGAAACACUC | GAGAAGCGGC | GGAAAACACC | GUGCGGCUGC | 480 |
| CCGGACCCAG | GCGCCACCCG | UUCUUCAUCG | GCUCUCCAGC | CGGCCUUGAG | CGCCCCGGCC | 540 |
| GGCCACCACC | CGCCGAAAAC | CGGGACCAAG | GAUUCACCGG | GUUCGUGACC | GUAUUGCGGA | 600 |
| GUGGGAUCCC | GGGGAUGGGA | UGCCGGAUGG | AUUUCUGAGC | AGGCGUCGCC | CGGCAGCCGA | 660 |
| CGGGCCGUGG | CCGGAACCGG | CCGGGCCGGU | CGGCGGGGUG | UGCGCGGUGC | CGGCCGAAGG | 720 |
| CGUGGGCCGG | AGCGCGGACC | CGAGCGCCGU | GUCAGCGCCG | UGUCAGGGCU | UUGGGGGCGC | 780 |
| GCCCUCACAU | ACUCGACCCG | CGUUCACGGA | GAGGAAGGCA | GGGAAGGGCC | CGUCCGCACC | 840 |
| GCGACCGGUG | CCGGCGCCCC | CGCCCGAUGC | CCGGCGCCGC | CCCACCGAGC | CGGACGCACC | 900 |
| GGAGGUUCCC | ACCGCCCGGC | CGGACGCCGG | CGUGCCGUUC | AGCCGGUGCG | CGGGCCGGCC | 960 |
| CGAGAUCUCA | CACCACUGGA | GAGCCAUGUC | ACGUCGCCUG | UUCACCUCGG | AGUCCGUGAC | 1020 |
| CGAGGGCCAC | CCCGACAAGA | UCGCCGACCG | GAUCAGCGAC | ACCGUCCUCG | AUGCCCUGCU | 1080 |
| CGCCCGGGAC | CCGCGGGCCA | GGUCGCCGU | CGAGACCCUG | AUCACCACCG | GUCAGGUCCA | 1140 |
| UAUCGCCGGC | GAGGUCACCA | CCACCGCGUA | CGCGCCCAUC | GCCCAACUGG | UGCGCGACAC | 1200 |
| CGUCCUGUCC | AUCGGCUACG | ACUCCUCGGC | CAAGGGCUUC | GACGGCGCCU | CGUGCGGGGU | 1260 |
| GUCGGUCUCC | AUCGGCGCGC | AGUCCCCGGA | CAUCGCCCGG | GGUGUGGACA | CCGCGUACGA | 1320 |
| GCGGCGGGGC | GGGGGCACGG | CCCCGGGCGG | ACCGGGUGAC | GAGCUGGACC | GGCAGGGCGC | 1380 |
| GGGCGACCAG | GGCUGAUGU | UCGGCUACGC | CUGCGACGAG | ACCCCCGAGC | UGAUGCCGCU | 1440 |
| GCCGAUCAAC | CUGGCGCACC | GGCUCUCCCG | GCGGCUGUCG | GAGGUGCGGA | AGAACGGCAC | 1500 |

-continued

```
GAUCCCCUAC CUCCGCCCCG ACGGCAAGAC CCAGGUCACC AUCGAGUACG ACGGCGACAA   1560
GGCGGUCCGC CUCGACACGG UCGUGGUCUC CUCCCAGCAC GCCUCCGGCA UCGACCUGGA   1620
CUCGCUACUG GCGCCCGACA UCCGCCGGCA UGUCGUGGAG CCCGUCCUCG CCGGACUGGC   1680
CGAGGACGGC AUCAAGCUGG ACACCGCGGG CUACCGGCUG CUGGUCAAUC CCACCGGCCG   1740
GUUCGAGAUC GGCGGCCCGA UGGGCGACGC GGGCCUGACC GGCCGCAAGA UCAUCAUCGA   1800
CACCUACGGC GGCAUGGCCC GGCAUGGCGG CGGUGCCUUC UCCGGCAAGG ACCCGUCCAA   1860
GGUGGACCGU CGGCGGCGU ACGCAAUGCG CUGGGUGGCC AAGAACGUCG UGGCGGCGGG   1920
GCUGGCCUCG CGGUGUGAGG UGCAGGUCGC CUACGCCAUC GGCAAGGCCG AGCCGGUCGG   1980
UCUGUUCGUG GAGACCUUCG GCACCGCCAC CGUGGACGUG GAGCGGAUCG AGCAGGCGAU   2040
CGGCGAGGUC UUCGACCUCC GCCCGGCCGC GAUCAUCCGG GAUCUGGACC UGCUCCGCCC   2100
GAUCUACGCC AAGACCGCCG CCUACGGCCA CUUCGGCCGC GAACUGCCCG AGUUCACCUG   2160
GGAACGCACC GACCGCACCG AGCAGCUCAU CGCCGCGGCC GGCCUCUGAA CCGGCCGACG   2220
UACCCCGAG GAGUCCUCAC GUGCGCAUCG CCGUCACCGG UUCCAUCGCC ACCGAUCACC   2280
UCAUGGCCUU UCCCGGCCGG UUCGGGGACC AGCUGAUCCC CGAUCAGCUC GCCCGGGUCU   2340
CGCUGUCUUU CCUCGUCGAC GGGCUCGAGG UGCGCCGGGG CGGAGUGGCC GUCGGCAUCG   2400
CCUUCGGCCU GGGCCGUCCG GGCCCCACGC CGCUGCUCGU CGGCGCCGUG GGGAACGACU   2460
UCGCCGACUA CGGGACCUGG CCGAAGGAGC ACGGCGUCGA CACCGGAGGC GUUCUGGUCC   2520
CGACCGAGCA CCAGACCGCC CGCUUCCUGU GCAUCACCGA CCGGGACGCC AACCAGAUCG   2580
CGGCCUCCUA CACGGGUGCG AUGCGGGAGG CCCGGGACAU CGGCCUGCGG CGGACGGGCG   2640
CUCUGCCGGC GCCCCGGCAC GGUCGGGUCC UCAUCUGCCC CGACGACCCG GCGGCGAUGG   2700
UGCGCCACAC CGCGCAGUGC CGGGAGCCGG GCCUGCCGUU CGUCGCCGAC CCCUCCCAGC   2760
AGCUCGCCCG GCUGGAGACG GACGAGGUAC GCGCGCUGGU GCACGGCGCC CACUGGGUCU   2820
UCACCAACGA GUACGAGGCC GCGCUGCUGC UCGAGCACUC CGGCUGGAAA CACUCCGAGA   2880
CCCUGGAACG GGUGGGCGCC UGGGUCACCA CGCUCGGCGG UGCCGGGGUC CGGAUCGAGC   2940
GCGCGGGCGA GCCACCGCUG ACGGUGCCCG CGGUCCCCGA UGUCCCCGUG GUCGAUCCGA   3000
CCGGGAUCGG UGCCGCCUUC CGGGCCGGUU CCUGGCCGG CGCCGGGCGC GGCCUUUCCA   3060
UCGUCUCCGC CGCCCGCCUG GGCUGCGUCC UGGCGGCGCG GGCGCUGGGG ACGGUCGGCC   3120
CCGCAGACCU ACCGGACCGA UCCGGCGGAU CCGCUCGCCA CGGCGAGGGA CGCGUACGGC   3180
GCGGACGCGG CGGCGCGGCU CGCCCUCGGG CUGGGCGGCC GCACAUGACC CGGCCCUGUC   3240
CCGGCUCCCG CGCGAGCCA CCGGCCGGAC GCCCGGCACG GCCGCCGCC GUCAUCCGCC   3300
GCCCCGGCGC CGGCGGGCCG ACCGCGGGAG GCUGCCGGUG AGGACCACCC UGCGCGAGAU   3360
CCUCGGCAGC GGCCGGUCU CCUUCUCCCA CGAGUUCUUC CCCCCGAGGA CGGAGGCCGG   3420
CACGCGGACG CUCUGGAACG CGAUCCGCCG GAUCGAACCG CUGGCCCCGA CCUUCGUCUC   3480
GGUCACCUAC GGCGCCGGCG GCUCCUCCCG GGACCGCACC GUCGAGGUCA CCAAGCGCAU   3540
CGCCACCGAC ACCACCCUGC GGCCGGUCGC CCAUCUCACC GCCGUCGGCC ACUCCGUCGC   3600
CGAACUGCGC CGCAUCAUCG GCCAGUACGC GGACGCCGGU GUCCGGGACG UACUCGCCCU   3660
GCGCGGCGAC CCGCCGGGGG AUCCGAACGC GCCCUGGGUC CCGCAUCCCG AGGGCUCAC   3720
CCACGCCCAU GAACUCGUCU CGCUGGUGCG CGGAUCGGGC GGCUUCGGUG UGGGCGUCGC   3780
GGCCUUCCCC GAGCGUCAUC CCCGUUCCCC CGACUGGGAC AGCGAGAUCC GGCACUUCGU   3840
GCGCAAGUGC CGGGCCGGCG CCGACUACGC CAUCACGCAG AUGUUCUUCC GGGUCGAGGA   3900
```

| | | | | |
|---|---|---|---|---|
|CUAUCUGCGG|CUGCGGGACC|GGGUCGCGGC|CGCCGGCUGC|UGCACCCCGG UCAUCCCCGG 3960|
|GAUCAUGCCC|GCCACCGACG|UGCGGCAGAU|CGCGCGCUUC|GCCGAGCUUU CCCACGCCAC 4020|
|CUUCCCCGAA|GGUCUCGCGC|GGCGGCUGGA|GGCCGCCCGC|GGCAACCCGG CCGAGGGACA 4080|
|CCGCAUCGGG|GUCGAGUACG|CCACCGCCAU|GGCCGGCCGG|CUGCUCGCCG AAGGCGCCCC 4140|
|GGGACUGCAC|UACAUCACUC|UCAACCGCUC|CACCGCGACG|UUGGAGAUCC ACCGGAACAU 4200|
|CCUGGGCACA|CCAGCCCCGG|GGAGUGCCCG|GCAGGUCCUC|GCGGCUCCCC UCUGACCGGC 4260|
|GGGGACCUCU|CGGCCCGGCC|CGCACGGCGG|CGGGCCCCGG|CUGCGCUCCC CCGGGUCGGG 4320|
|UCCGGCCCGC|CGUCCCGGCC|GCCGUCCGGG|CCGGCGGCGG|CGGACCGUGC GCGGGCGAAG 4380|
|CACACCGCCG|CGCGUUUCCC|CCGGGUCCCG|GCGCCGCGGG|CGGCCCCGGC GCCGGAACCC 4440|
|GGCCGUCCGC|UCGCCGCGCC|CCCCCGGGGG|GGGACGGCCG|GACGGCCCUC UUCCGGGACG 4500|
|GCACUCAGCG|UCCGCCGGAG|ACGACGCCCU|CGCGCAGCUC|CAGAUGCGAG CCGGUGAACC 4560|
|GGCUUCGCAU|CCGCCGGUCG|UGGGUGACCA|GCACCAGCGC|GCCCCGUAG CCCGUCAGCG 4620|
|CCUCCUCCAA|CUCCUCCACC|AGCGCCGGUG|AGAGGUGGUU|GGUGGGCUCG UCCAGCAGGA 4680|
|GCAGACCCAC|CGGCUCGCUG|ACCAGCCGGG|CCAGUUCGAU|GCGGCGGCGC UGACCGUACG 4740|
|ACAGCUCCCC|GACCCGCAGC|CGCAGCGCCU|CCGGCUCGAA|CAGGCCGAGG GACAGCAGCC 4800|
|GGUCGGCCUG|UUCGUCCCGG|UCGCCGGGCC|GGUUGUGGGC|GAAGGCCU 4848|